(12) United States Patent
Utagawa

(10) Patent No.: US 9,339,183 B2
(45) Date of Patent: May 17, 2016

(54) ABERRATION CORRECTION METHOD, PHOTOGRAPHING METHOD AND PHOTOGRAPHING APPARATUS

(71) Applicant: CANON KABUSHIKI KAISHA, Tokyo (JP)

(72) Inventor: Tsutomu Utagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/200,170

(22) Filed: Mar. 7, 2014

(65) Prior Publication Data

US 2014/0185008 A1 Jul. 3, 2014

Related U.S. Application Data

(62) Division of application No. 13/456,582, filed on Apr. 26, 2012, now Pat. No. 8,708,489.

(30) Foreign Application Priority Data

May 10, 2011 (JP) ................................. 2011-105386

(51) Int. Cl.
*A61B 3/14* (2006.01)
*A61B 3/00* (2006.01)
*A61B 3/12* (2006.01)

(52) U.S. Cl.
CPC .... *A61B 3/12* (2013.01); *A61B 3/14* (2013.01)

(58) Field of Classification Search
USPC ................................................ 351/200–246
See application file for complete search history.

(56) References Cited

U.S. PATENT DOCUMENTS

2004/0227978 A1* 11/2004 Enomoto ...................... 358/3.26
2012/0218516 A1* 8/2012 Imamura ....................... 351/206
2013/0070202 A1* 3/2013 Yonezawa et al. ............ 351/206
2013/0321765 A1* 12/2013 Yuasa .......................... 351/206

FOREIGN PATENT DOCUMENTS

JP 2009-207572 A 9/2009

OTHER PUBLICATIONS

Yan Zhang, et al., "High-speed volumetric imaging of cone photoreceptors with adaptive optics spectral-domain optical coherence tomography", Optics Express, vol. 14, No. 10, May 15, 2006, pp. 4380-4394.
Yan Zhang, et al. article.

* cited by examiner

*Primary Examiner* — Mohammed Hasan
(74) *Attorney, Agent, or Firm* — Fitzpatrick, Cella, Harper & Scinto

(57) ABSTRACT

A fundus image photographing apparatus with adaptive optics generally corrects an aberration by feedback control using a wave front sensor and a wave front correction device. The reduction in the time required to correct the aberration to a high-resolution photographing level is demanded. Aberration correction information of last photographing is stored for each subject, and a stored correction value is used to correct the aberration to reduce the time before the completion of the aberration correction. If there is no stored information, a correction value for a preset reference aberration amount is used.

24 Claims, 9 Drawing Sheets

ABERRATION CORRECTION METHOD, PHOTOGRAPHING METHOD AND PHOTOGRAPHING APPARATUS

This application is a division of application Ser. No. 13/456,582 filed Apr. 26, 2012 now U.S. Pat. No. 8,708,489 B2.

BACKGROUND OF THE INVENTION

1. Field of the Invention

The present invention relates to a fundus image photographing method and a fundus image photographing apparatus, and particularly, to an aberration correction method that has an adaptive optics function of measuring and correcting an aberration of an eye to be inspected and that is for correcting the aberration according to a situation of acquisition of a photographed image, a fundus image photographing method that can correct an aberration based on the method, and a fundus image photographing apparatus.

2. Description of the Related Art

In recent years, an SLO (Scanning Laser Ophthalmoscope) that two-dimensionally directs a laser beam to the fundus to receive reflected light to form an image and an imaging apparatus that uses interference of low-coherence light are developed as ophthalmic photographing apparatuses. The imaging apparatus using the interference of the low-coherence light is called an OCT (Optical Coherence Tomography), which is particularly used to obtain a tomographic image of the fundus or near the fundus. Various types of the OCT are developed, such as a TD-OCT (Time Domain OCT) and an SD-OCT (Spectral Domain OCT).

Particularly, the resolution is further improving in the ophthalmic photographing apparatuses in recent years, due to a high NA of an illumination laser.

However, the fundus needs to be photographed through optical parts of the eye, such as cornea and crystalline lens. Therefore, the aberration of the cornea and the crystalline lens significantly affects the image quality of the photographed image along with the improvement in the resolution.

Consequently, the research of an AO-SLO and an AO-OCT that include an optical system with an adaptive optics (AO) function for measuring the aberration of the eye to correct the aberration is in progress. For example, "Y. Zhang et al, Optics Express, Vol. 14, No. 10, 15 May 2006" illustrates an example of the AO-OCT. The AO-SLO and the AO-OCT generally measure the wave front of the eye based on a Shack-Hartmann wave front sensor system. The Shack-Hartmann wave front sensor system is a system in which measuring light is directed to the eye, and a CCD camera receives reflected light through a microlens array to measure the wave front. A deformable mirror and a spatial phase modulator are driven to correct the measured wave front. The AO-SLO and the AO-OCT can photograph the fundus through the deformable mirror and the spatial phase modulator to perform high-resolution photographing.

In the AO used in an ophthalmic apparatus, the aberration measured by the wave front sensor is generally modeled by a function such as a Zernike function, and the function is used to calculate a correction amount of a wave front corrector. To correct a complicated shape, the aberration needs to be modeled by a high-order function to calculate the correction amount to control the wave front corrector.

However, the calculation of the correction amount imposes a significantly high calculation load, and an increase in the calculation time is a major problem. Particularly, periodical observation of the diseased part is requested for the ophthalmic apparatus to follow up the illness. Therefore, some reduction in the photographing time is essential to improve the efficiency of the ophthalmic medical treatment.

SUMMARY OF THE INVENTION

In view of the foregoing problem, an object of the present invention is to reduce time required for aberration correction of an eye in an ophthalmic apparatus using an AO.

To solve the problem, the present invention provides an aberration correction apparatus that corrects an aberration of an object, the aberration correction apparatus comprising: a selection unit configured to select aberration information if a storage unit stores information related to the aberration of the object and to select information similar to the aberration information from information stored in the storage unit if the storage unit does not store the aberration information of the object; an aberration correction unit configured to handle one of the aberration information and the similar information selected by the selection unit as new information and to correct the aberration of the object based on the new information; and a storage control unit configured to store the new information related to the corrected aberration of the object in the storage unit.

According to the present invention, the information of the last photographing can be used to speed up the aberration correction, and the time required for the diagnosis can be reduced.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Modes for carrying out the present invention will be described based on the following embodiments. However, the present invention is not limited to the configurations of the following embodiments in any sense.

First Embodiment

A configuration of a fundus image photographing apparatus applying the present invention will be described as a first embodiment with reference to FIG. 1.

The present embodiment describes an example in which an eye is an object to be measured, and an adaptive optics system corrects an aberration generated in the eye to photograph the fundus.

Figure 1:
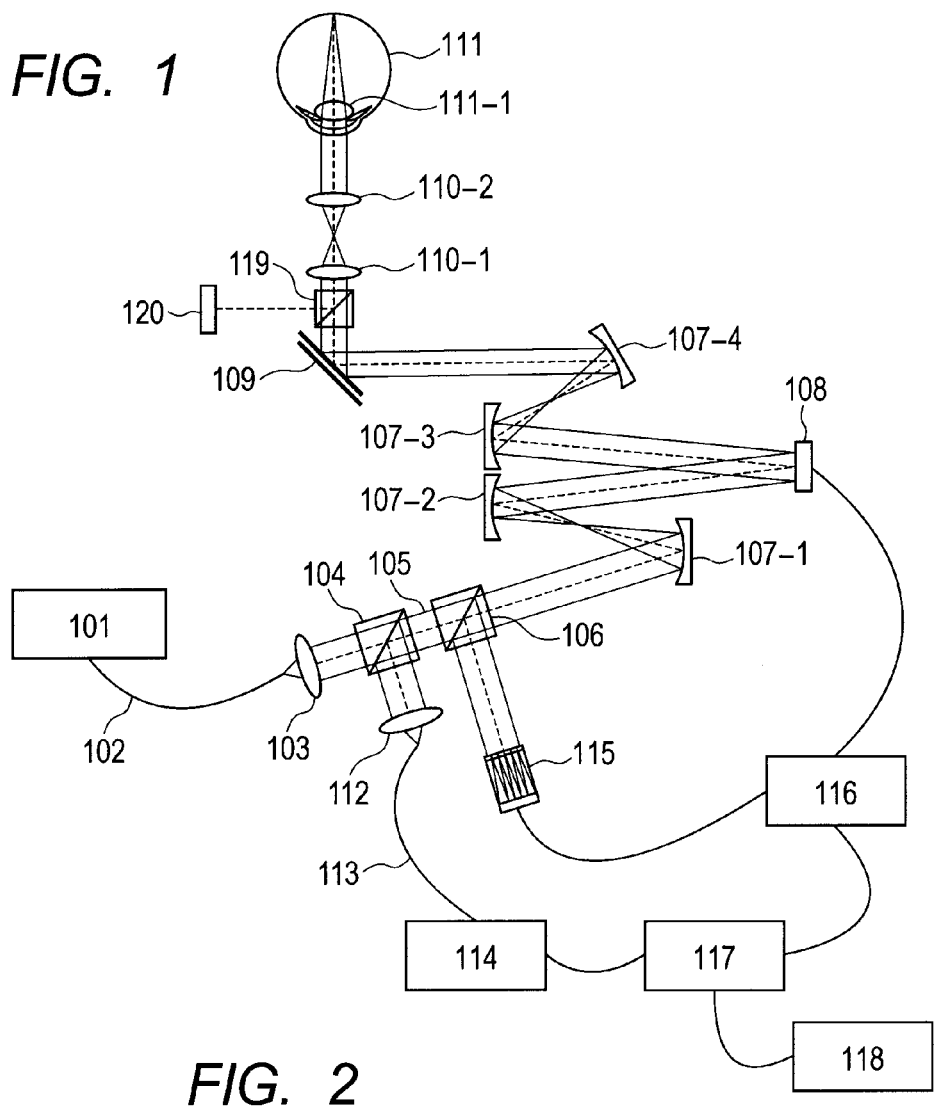
FIG. 1 is a schematic diagram of an example of a configuration of a fundus image photographing apparatus based on an SLO with an adaptive optics system according to a first embodiment of the present invention.

In FIG. 1, reference numeral 101 denotes a light source, and an SLD light source (Super Luminescent Diode) with a wavelength of 840 nm is used. Although the wavelength of the light source 101 is not particularly limited, a thickness of about 800 to 1500 nm is suitably used for the fundus image photographing to alleviate the brightness for the subject and to maintain the resolution. Although the SLD light source is used in the present embodiment, a laser can also be used. Although the light source is used both in the fundus image photographing and wave front measurement in the present embodiment, separate light sources may be provided, and the light may be multiplexed in the middle of the optical path.

Light directed from the light source 101 passes through a single-mode optical fiber 102, and a collimator 103 outputs parallel light (measuring light 105).

The output measuring light 105 transmits through a light divider 104 including a beam splitter and is guided to an optical system of adaptive optics.

The adaptive optics system includes a light divider 106, a wave front sensor 115, a wave front correction device 108, and reflective mirrors 107-1 to 107-4 that guide light to the components.

The reflective mirrors 107-1 to 107-4 are arranged so that at least the pupil of an eye 111, the wave front sensor 115 and the wave front correction device 108 are optically conjugate. A beam splitter is used as the light divider 106 in the present embodiment.

The reflective mirrors 107-1 and 107-2 reflect the measuring light 105 transmitted through the light divider 106, and the measuring light 105 enters the wave front correction device 108. The measuring light 105 reflected by the wave front correction device 108 is output to the reflective mirror 107-3.

Figure 2:
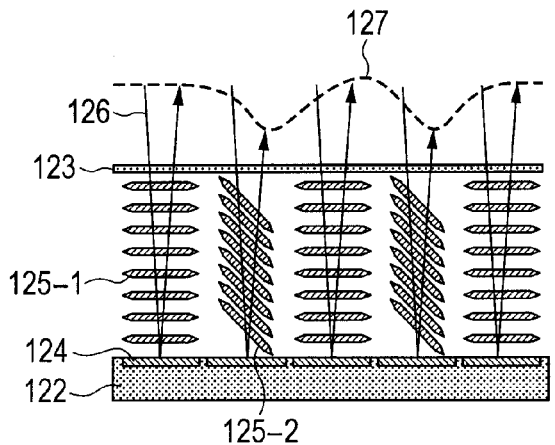
FIG. 2 is a schematic diagram illustrating an example of a wave front correction device according to the first embodiment of the present invention.

A spatial phase modulator using a liquid crystal element is used as the wave front correction device 108 in the present embodiment. FIG. 2 illustrates a schematic diagram of a reflective liquid crystal optical modulator. In the modulator, liquid crystal molecules 125 are enclosed in a space between a base section 122 and a cover 123. The base section 122 includes a plurality of pixel electrodes 124, and the cover 123 includes transparent opposing electrodes not illustrated. The liquid crystal molecules are aligned as illustrated by reference numeral 125-1 when a voltage is not applied between the electrodes. The alignment changes to a state as illustrated by reference numeral 125-2 when a voltage is applied, and the refractive index relative to the incident light changes. Spatial phase modulation is possible by controlling the voltage of each pixel electrode to change the refractive index of each pixel. For example, when incident light 126 enters the modulator, the phase of the light passing through the liquid crystal molecules 125-2 lags behind the phase of the light passing through the liquid crystal molecules 125-1. As a result, a wave front as illustrated by reference numeral 127 in FIG. 2 is formed. In general, the reflective liquid crystal optical modulator includes several tens of thousands to several hundreds of thousands of pixels. The liquid crystal optical modulator has polarization characteristics, and the modulator may include a polarization element that adjusts the polarization of the incident light.

Figure 3:
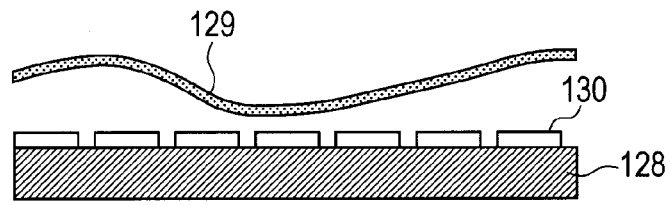
FIG. 3 is a schematic diagram illustrating another example of the wave front correction device.

Another example of the wave front correction device 108 includes a deformable mirror. The deformable mirror can locally change the reflection direction of the light, and the deformable mirror is implemented in various systems. FIG. 3 illustrates an example of a cross section of another wave front correction device 108. The wave front correction device 108 includes a deformable film-like mirror surface 129 that reflects incident light, a base section 128, actuators 130 arranged between the mirror surface 129 and the base section 128, and a support not illustrated that supports the mirror surface 129 from the surrounding. Examples of the principle of operation of the actuators 130 include the use of electrostatic force, magnetic force, and a piezoelectric effect, and the configuration of the actuators 130 varies depending on the principle of operation. A plurality of actuators 130 are two-dimensionally arranged on the base section 128. The actuators 130 can be selectively driven to freely deform the mirror surface 129. In general, the deformable mirror includes several tens to several hundreds of actuators.

Figure 9:
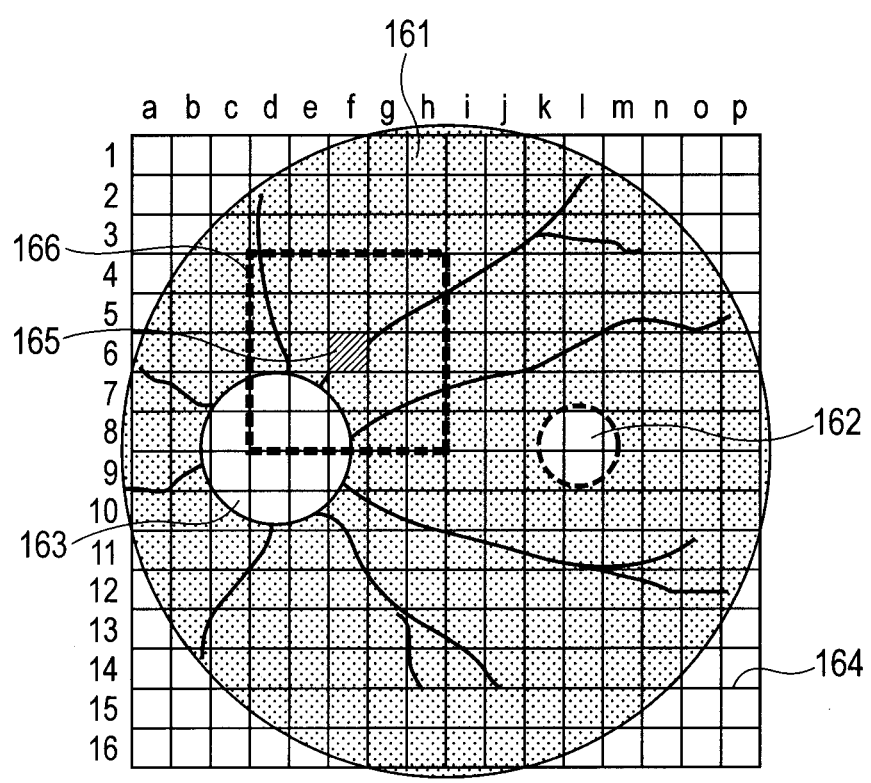
FIG. 9 is a diagram describing photographing areas dividing the fundus into a grid.

In FIG. 1, a scanning optical system 109 one-dimensionally or two-dimensionally scans the light reflected by the reflective mirrors 107-3 and 107-4. In the present embodiment, two galvano scanners for main scanning (horizontal direction of fundus) and for sub scanning (vertical direction of fundus) are used in the scanning optical system 109. A resonant scanner for main scanning of the scanning optical system 109 may also be used for faster photographing. Optical elements, such as mirrors and lenses, may be used between the scanners in the apparatus to optically conjugate the scanners in the scanning optical system 109. FIG. 9 illustrates a state in which a fundus image photographing apparatus divides and photographs the fundus of the eye to be inspected. Reference numeral 161 denotes a two-dimensional image of the fundus. Reference numeral 162 denotes macula, and reference numeral 163 denotes optic papilla. Reference numeral 164 denotes a state in which the fundus 161 is divided into a grid. Addresses of a to p and 1 to 16 are allocated to the horizontal direction and the vertical direction, respectively. The fundus is divided into 256 pieces (16×16), and the fundus is photographed area by area.

The scanning optical system 109 reads each section by dividing the section into 256×256 pixels (3 µm pieces) in the main scanning direction and the sub scanning direction.

The measuring light 105 scanned by the scanning optical system 109 is directed to the eye 111 through eyepieces 110-1 and 110-2. Reference numeral 111-1 denotes a crystalline lens equivalent to the lens of the eye.

The fundus reflects or scatters the measuring light directed to the eye 111. The positions of the eyepieces 110-1 and 110-2 can be adjusted for optimal irradiation according to the diopter scale of the eye 111. Although lenses are used for the eyepiece sections, spherical mirrors may also be used.

Figure 7:
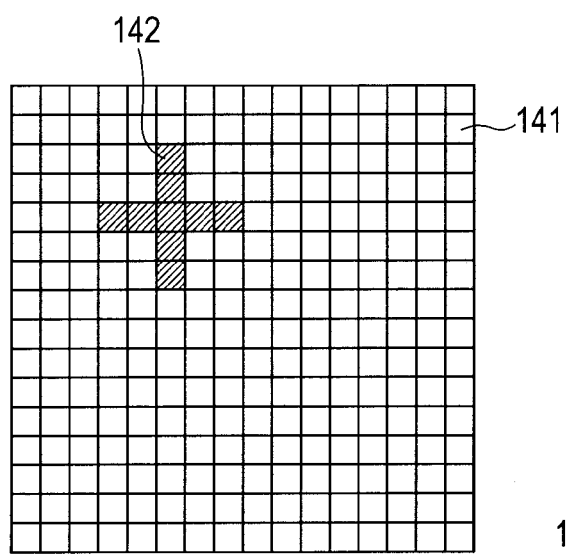
FIG. 7 is a diagram describing a fixation lamp.

Reference numeral 119 denotes an optical spectroscope that is a beam splitter, and reference numeral 120 denotes a fixation lamp. The beam splitter 119 guides the light from the fixation lamp 120 to the eye to be inspected along with the measuring light 105. The fixation lamp 120 instructs the subject for the direction of the eyes, and the fixation lamp 120 includes a crystal display and an LED arranged in a grid on a plane. FIG. 7 shows an enlarged view of a liquid crystal display 141 included in the fixation lamp 120. As illustrated in FIG. 7, a cross as illustrated by reference numeral 142 is lit on the liquid crystal display 141. The subject is asked to view the intersection of the cross 142, and the movement of the eye to be inspected can be stopped. The lighting position of the cross 142 can be vertically and horizontally moved on the liquid crystal display 141 to control the line of sight of the subject to observe a desired area of the eye to be inspected.

The reflected light reflected or scattered from the retina of the eye 111 advances through the path in the direction opposite the direction when the light has entered. The light divider 106 reflects part of the light to the wave front sensor 115, and the light is used to measure the wave front of the light beam.

Figure 4A:
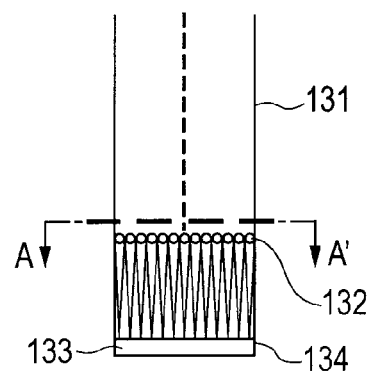
FIGS. 4A and 4B are schematic diagrams illustrating a configuration of a Shack-Hartmann sensor.
Figure 4B:
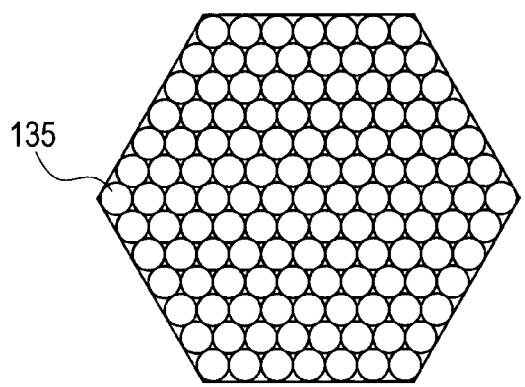
Figure 5:
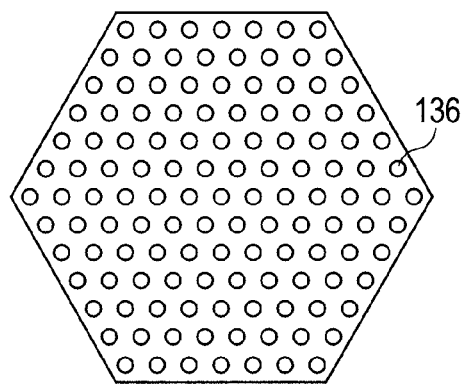
FIG. 5 is a schematic diagram illustrating a state of a light beam for measuring a wave front concentrated on a CCD sensor.
Figure 6A:
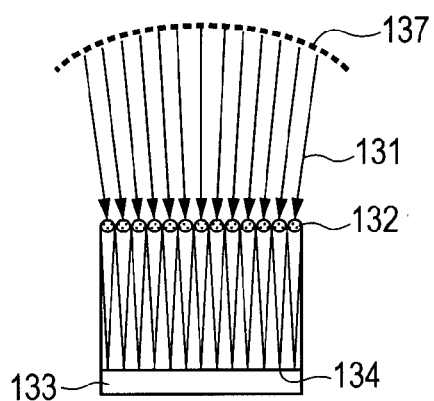
FIGS. 6A and 6B are schematic diagrams when a wave front with a spherical aberration is measured.
Figure 6B:
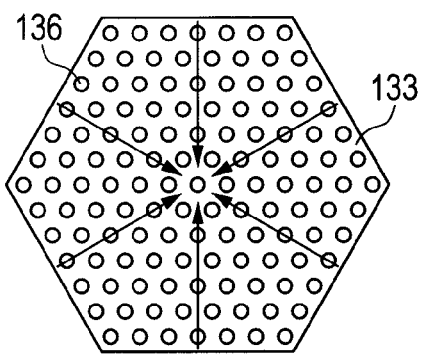

In the present embodiment, a Shack-Hartmann sensor is used as the wave front sensor 115. FIGS. 4A and 4B illustrate schematic diagrams of the Shack-Hartmann sensor. Reference numeral 131 denotes a light beam for measuring the wave front, and the light beam is concentrated on a focal plane 134 over a CCD sensor 133 through a microlens array 132. FIG. 4B is a diagram illustrating a state viewed from a position indicated by A-A' of FIG. 4A. FIG. 4B illustrates that the microlens array 132 includes a plurality of microlenses 135. The light beam 131 is concentrated on the CCD sensor 133 through the microlenses 135. Therefore, the light beam 131 is divided into spots equivalent to the number of the microlenses 135 and is concentrated. FIG. 5 illustrates the concentration of the light on the CCD sensor 133. The light beams passed through the microlenses are concentrated on spots 136. The wave front of the incident light beam is calculated from the positions of the spots 136. FIG. 6A illustrates a schematic diagram when a wave front with a spherical aberration is measured. The light beam 131 is formed by a wave front as illustrated by reference numeral 137. The microlens array 132 concentrates the light beam 131 at local positions of the wave front in the perpendicular direction. FIG. 6B illustrates the concentration of light in the CCD sensor 133. Since the light beam 131 has the spherical aberration, the spots 136 are concentrated toward the center. The positions can be calculated to detect the wave front of the light beam 131. Although the Shack-Hartmann sensor is used as the wave front sensor in the present embodiment, the sensor is not limited to this. Another wave front measurement unit, such as a curvature sensor, and a method of obtaining the wave front through inverse calculation of a formed point image can also be used.

In FIG. 1, the light divider 104 reflects part of the reflected light transmitted through the light divider 106, and the reflected light is guided to a light intensity sensor 114 through a collimator 112 and an optical fiber 113. The light intensity sensor 114 converts the light to an electrical signal. A control unit 117 forms a fundus image, and a display 118 displays the fundus image.

The wave front sensor 115, which is connected to an adaptive optics control unit 116, transmits the received wave front to the adaptive optics control unit 116. The wave front correction device 108, which is also connected to the adaptive optics control unit 116, performs modulation instructed by the adaptive optics control unit 116. The adaptive optics control unit 116 calculates a modulation amount (correction amount) for making a correction to form a wave front without aberration based on the acquired wave front according to the measurement result of the wave front sensor 115 and commands the wave front correction device 108 for the modulation. The measurement of the wave front and the instruction to the wave front correction device are repeated, and the feedback is controlled to always form an optimal wave front.

In the present embodiment, the measured wave front is modeled by a Zernike function to calculate coefficients of each order, and the modulation amount of the wave front correction device 108 is calculated based on the coefficients. In the calculation of the modulation amount, based on a reference modulation amount for the formation of the shapes of each Zernike order by the wave front correction device, the wave front correction device multiplies the measured coefficients of all Zernike orders by the reference modulation amount and further integrates the results to obtain a final modulation amount.

As described, in the present invention, the wave front corresponding to the aberration amount is expressed using the Zernike function which is a predetermined function. The Zernike function is an example, and various other functions expressing the wave front can also be used.

A reflective liquid crystal spatial phase modulator with 600×600 pixels is used as the wave front correction device 108 in the present embodiment, and the modulation amount of each of the 360000 pixels is calculated according to the calculation method. For example, in the calculation using first to fourth order coefficients of the Zernike function, fourteen coefficients of $Z1-1$, $Z1+1$, $Z2-2$, $Z2-0$, $Z2+2$, $Z3-3$, $Z3-1$, $Z3+1$, $Z3+3$, $Z4-4$, $Z4-2$, $Z4-0$, $Z4+2$ and $Z4+4$ are multiplied by the reference modulation amount for the 360000 pixels. In the calculation using first to sixth order coefficients of the Zernike function, twenty seven coefficients of $Z1-1$, $Z1+1$, $Z2-2$, $Z2-0$, $Z2+2$, $Z3-3$, $Z3-1$, $Z3+1$, $Z3+3$, $Z4-4$, $Z4-2$, $Z4-0$, $Z4+2$, $Z4+4$, $Z5-5$, $Z5-3$, $Z5-1$, $Z5+1$, $Z5+3$, $Z5+5$, $Z6-6$, $Z6-4$, $Z6-2$, $Z6-0$, $Z6+2$, $Z6+4$ and $Z6+6$ are multiplied by the reference modulation amount for the 360000 pixels. Although low-order aberrations, such as nearsight, far-sight and astigmatism, account for a large portion of the aberration of the eye, there are also other higher-order aberrations caused by minute unevenness of the optical system of the eye or caused by disorder of a tear film. When the aberration of the eye is expressed by the Zernike function system, second-order Zernike functions, which indicate nearsight, far-sight and astigmatism, account for a large portion. Some third-order Zernike functions and fourth-order Zernike functions are included, and few high-order functions, such as fifth order and six order Zernike functions, are further included. The first to fourth order Zernike functions do not change much for the most part even after a lapse of time, except when the near-sight, the far-sight or the astigmatism rapidly progresses. If the cause of the aberration is near-sight, far-sight or astigmatism, the first to fourth Zernike functions do not vary much between the areas when the photographed areas are adjacent.

As described, the aberration amount obtained by the wave front measurement is expressed by predetermined functions in the present invention, and in that case, it is suitable if the aberration amount indicated by high-order functions is not included from the viewpoint of the calculation speed. The orders excluded from the calculation can be high-order functions of fifth or higher orders. The eye to be inspected is included in part of the optical system, and the optical system is in an uncertain state. Therefore, the acquisition of a wave front with a low aberration is generally difficult based only on one aberration measurement and correction. The aberration measurement and correction are repeated to correct the aberration to obtain an aberration that allows photographing.

Figure 8:
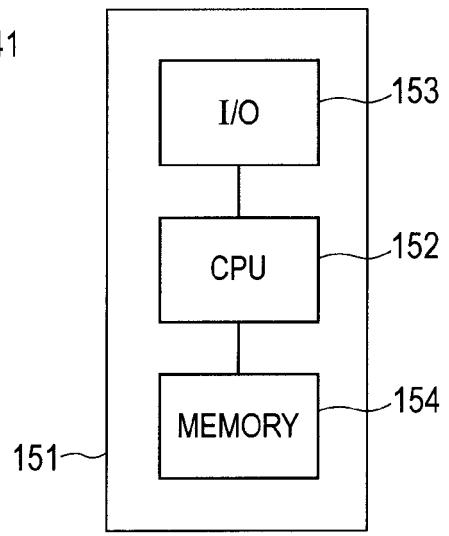
FIG. 8 is a diagram describing a controller.

A controller not illustrated controls the entire fundus image photographing apparatus illustrated in FIG. 1. FIG. 8 is a block diagram of the controller. As illustrated in FIG. 8, a controller 151 includes a CPU 152, an I/O control unit 153 and a memory 154. The CPU 152 controls the fundus image photographing apparatus according to a program included in the CPU 152. The memory 154 stores aberration information of the eye of the subject already photographed by the fundus image photographing apparatus, for each photographing area of the eye to be inspected. Specifically, an ID of the subject, an address (f, 6) of the photographing area as illustrated by reference numeral 165 of FIG. 9, and an aberration amount when the area is photographed are stored.

According to commands from the CPU 152, the I/O control unit 153 drives or controls communications of a mouse, a keyboard and a bar code reader not illustrated as well as the scanning optical system 109, the adaptive optics control unit 116 and the control unit 117.

Figure 10:
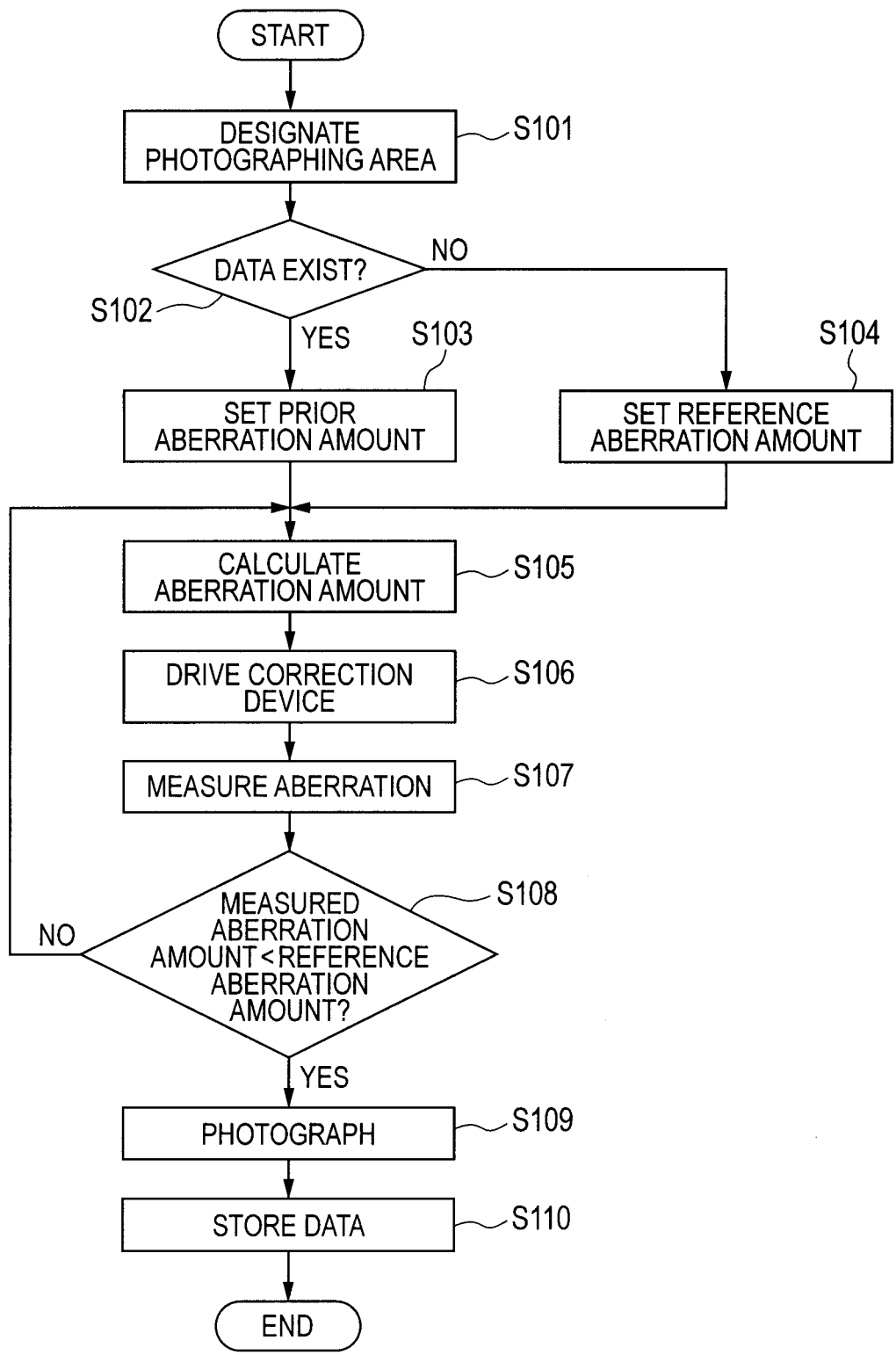
FIG. 10 is a flow chart illustrating a control step of the fundus image photographing apparatus according to the first embodiment of the present invention.

An operation of the present invention in the fundus image photographing apparatus with the configuration will be described with reference to the flow chart of FIG. 10. First, the mouse, the keyboard and the bar code reader not illustrated are used to designate a photographing area of the eye to be inspected for the subject (step 101, hereinafter "S101").

Whether the photographing area designated in S101 has been photographed is determined for the subject (S102). The process executed in the step corresponds to determining whether information related to the aberration of the eye to be inspected (also simply called "aberration information") is stored in advance according to the present invention. An area that functions as a determination unit of the present invention in the controller 151 executes the process. If the designated area has been photographed in the past, i.e. if the memory 154 stores the aberration information of the designated area, the aberration amount in the last photographing of the designated area, i.e. the coefficients of the orders in the model of the Zernike function, is set to the adaptive optics control unit 116 (S103). If the designated area has not been photographed in the past, i.e. if the memory 154 does not store the aberration information of the designated area, information related to the preset reference aberration amount and the aberration amount is set to the adaptive optics control unit 116 (S104). The case of first photographing of the subject is processed in the same way as the case in which the designated area has not been photographed in the past. The process corresponds to selecting information related to the aberration of the eye to be inspected if the information is stored in advance and selecting other information different from the information if the information is not stored according to the present invention. The area that functions as a selection unit in the controller 151 executes the process. The "other information" is also called "information similar to the aberration information" and is, for example, standard value information (such as the reference aberration amount) statistically created based on clinical data. The "information similar to the aberration information" is, for example, other aberration information in an adjacent area of the predetermined area of the eye to be inspected (photographing area of the eye to be inspected). In this case, the selection unit selects the other aberration information stored in the storage unit based on position information of the predetermined area of the eye to be inspected. More specifically, the selection unit selects the aberration information if the storage unit stores the aberration information of the eye to be inspected and selects the information similar to the aberration information from the information stored in the storage unit if the storage unit does not store the aberration information of the eye to be inspected.

The adaptive optics control unit 116 calculates a modulation amount (correction amount) for correcting the set aberration amount (S105) and commands the wave front correction device 108 for the modulation (S106). In the modulated state of S106, the wave front sensor 115 measures the aberration amount of the designated area of the subject (S107). Whether the measured aberration amount is smaller than a reference value is determined (S108). If the aberration amount is equal to or greater than the reference value, a modulation amount (correction amount) for correcting the aberration amount in this state is calculated (S105), and the process is repeated until the aberration amount becomes smaller than the reference value. When the aberration amount becomes smaller than the reference value, the designated area of the eye to be inspected is photographed (S109). Lastly, the latest aberration amount for the designated area is stored in the memory 154 (S110), and the photographing is finished. The process of correcting the aberration amount corresponds to correcting the aberration of the eye to be inspected based on the selected information or the other information according to the present invention. Areas that control the adaptive optics control unit 116, the wave front sensor 115 and the controller 151 execute the process, and the configurations function as an aberration correction unit according to the present invention. More specifically, the aberration correction unit handles the aberration information or the similar information selected by the selection unit as new information related to the aberration and corrects the aberration of the eye to be inspected based on the new information. The determination of whether the aberration amount has become smaller than the reference value corresponds to comparing the corrected aberration of the eye to be inspected with the reference value according to the present invention, and an area that functions as a comparison unit in the controller 151 executes the process.

The process of S110 for storing the latest aberration amount for the designated area corresponds to storing the new information related to the corrected aberration of the eye to be inspected as new information related to the aberration stored in advance according to the present invention, and the controller 151 executes the process. The controller 151 functions as a storage control unit that stores, in the memory 154 that functions as a storage unit, the new information related to the aberration of the eye to be inspected for which the aberration is corrected.

The information related to the aberration in the present invention includes areas defined by specific pixels in the image of the eye to be inspected, the resolution of the photographed images based on the pixels, and the aberration amount.

Figure 11:
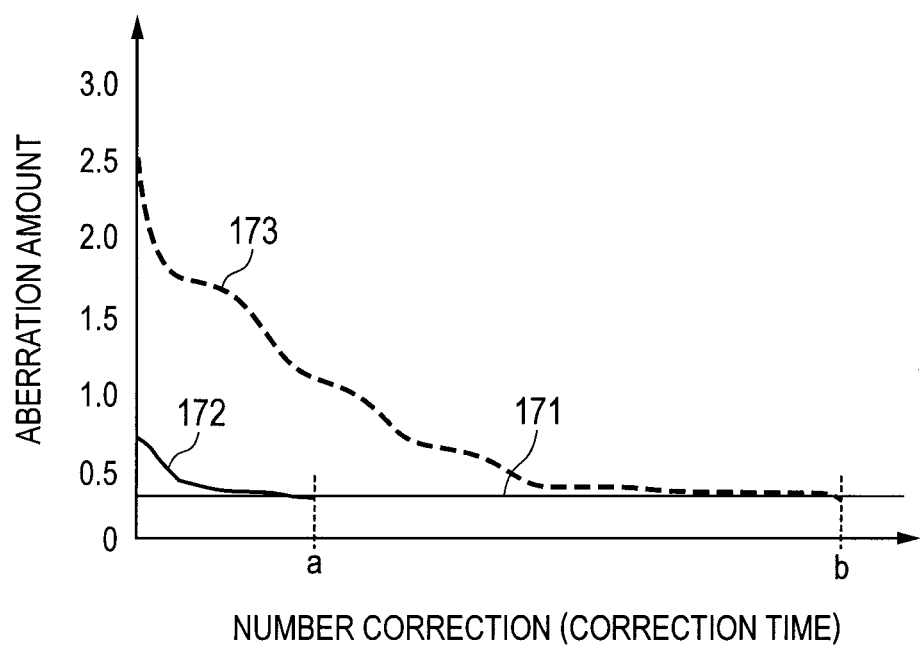
FIG. 11 is a graph indicating a relationship between the number of aberration corrections and an aberration amount.

FIG. 11 is a graph indicating a relationship between the number of aberration corrections and the aberration amount. The horizontal axis denotes the number of aberration corrections, i.e. the number of the loops of S105 to S108 of the flow chart of FIG. 10, which indicates the time required for the aberration correction. The vertical axis indicates the aberration amount. Reference numeral 173 denotes a curve indicating a state when the aberration is corrected by the conventional method, and reference numeral 172 denotes a curve indicating a state when the aberration is corrected by the method of the present invention. Reference numeral 171 denotes a reference value for comparing the size of the aberration amount in S108. As illustrated in FIG. 11, photographing is started at a correction time a when the aberration is corrected by the method of the present invention, and photographing is started at a correction time b when the aberration is corrected by the conventional method.

According to the present embodiment, the aberration information in the prior photographing can be used to reduce the time required for the aberration correction, and photographing is possible in a short time.

Second Embodiment

Figure 12:
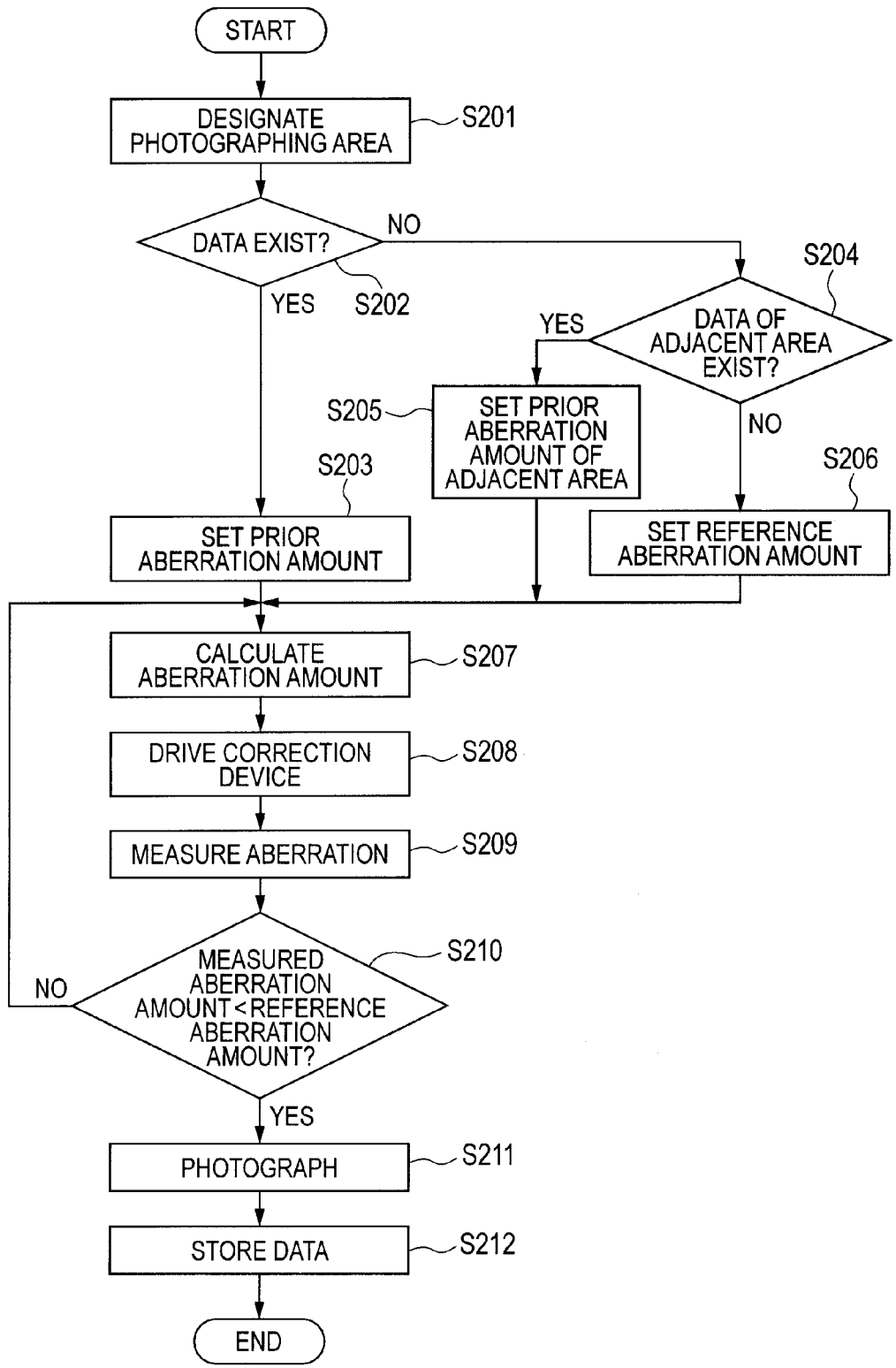
FIG. 12 is a flow chart illustrating a control step of the fundus image photographing apparatus according to a second embodiment of the present invention.

In a second embodiment, an example of a control method of the fundus image photographing apparatus in a mode different from the first embodiment applying the present invention will be described with reference to a flow chart of FIG. 12. In the present embodiment, the basic configuration of the apparatus is the same as in the first embodiment. Description of the same operation as in the first embodiment will not be repeated.

The present embodiment describes a method that is effective when an area to be photographed has not been photographed in the past, but an adjacent area has been photographed.

First, a mouse, a keyboard and a bar code reader not illustrated are used to designate a photographing area of an eye to be inspected for the subject (S201). Whether the photographing area designated in S201 has been photographed is determined for the subject (S202). If the designated area has been photographed in the past, i.e. if the memory 154 stores the aberration information of the designated area, the aberration amount in the last photographing of the designated area, i.e. the coefficients of the orders in the model of the Zernike function, is set to the adaptive optics control unit 116 (S203).

If the designated area has not been photographed in the past, whether an adjacent area has been photographed is determined (S204). An area of vertical and horizontal 5×5 areas around the designated area is defined as the adjacent area here. Specifically, if the address of the designated area 165 is (f, 6) as illustrated in FIG. 9, the adjacent area is an area 166 surrounded by areas of addresses (d, 4), (h, 4), (d, 8) and (h, 8). If the adjacent area has been photographed, i.e. if the memory 154 stores the aberration information of the designated area, the aberration amount when the closest area in the adjacent area is photographed, i.e. the coefficients of the orders in the model of the Zernike function, is set to the adaptive optics control unit 116 (S205). If the adjacent area of the designated area has not been photographed in the past, i.e. the memory 154 does not store the aberration information of the adjacent area of the designated area, the reference aberration amount is set to the adaptive optics control unit 116 (S206). The case of first photographing of the subject is processed in the same way as the case in which the designated area and the adjacent area of the designated area have not been photographed in the past. The process of S207 to S212 is the same as in the first embodiment.

Therefore, in the present embodiment, the information related to the previous aberration stored in advance for the most adjacent area of the area is selected as the other information to execute the following process if the information stored in advance for the area of the eye to be inspected for obtaining a fundus image does not exist at the start of the correction of the aberration of the eye to be inspected in the process of acquiring the information related to the aberration stored in advance.

According to the present second embodiment, the aberration information in the prior photographing of the adjacent area of the designated area can be used to reduce the time required for the aberration correction, and photographing is possible in a short time.

Third Embodiment

Figure 13:
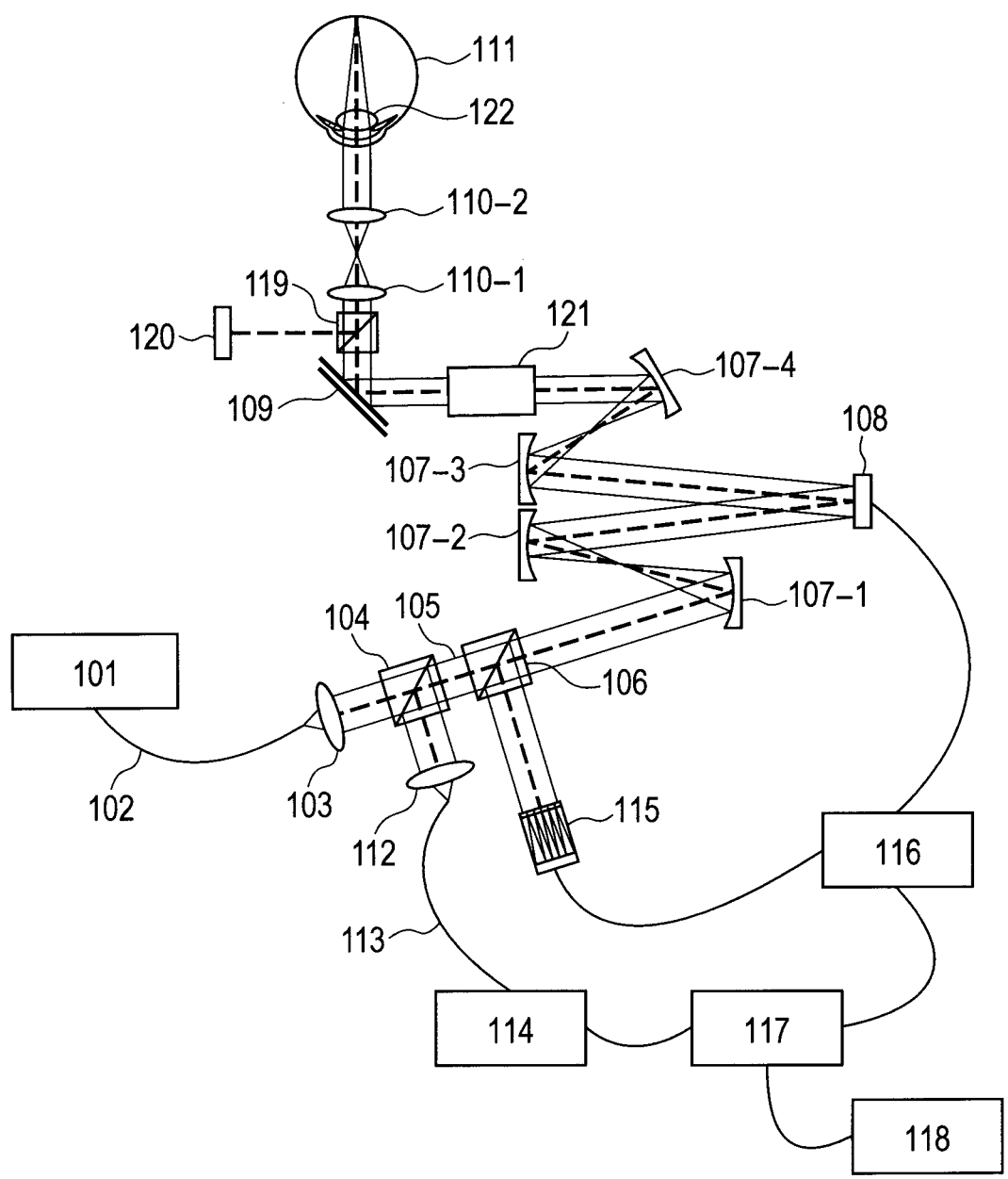
FIG. 13 is a schematic diagram of an example of a configuration of the fundus image photographing apparatus based on an SLO with an adaptive optics system according to a third embodiment of the present invention.

In a third embodiment, the apparatus including a resolution changing unit will be described. As illustrated in FIG. 13, a resolution changing unit 121 is arranged between the reflective mirror 107-4 and the scanning optical system 109. The resolution changing unit 121, which includes a plurality of lenses, changes a luminous flux diameter of the measuring light 105 directed to the crystalline lens 122 according to a control signal from a controller not illustrated to change a beam spot diameter on the fundus, i.e. the resolution of the photographed image. Specifically, the luminous flux diameter of the measuring light that passes through the crystalline lens 111-1 is enlarged to reduce the beam spot diameter on the fundus, i.e. to increase the resolution. The luminous flux diameter of the measuring light 105 that passes through the crystalline lens 111-1 is reduced to enlarge the beam spot diameter on the fundus, i.e. to reduce the resolution. If the luminous flux diameter of the measuring light 105 passing through the crystalline lens 111-1 is changed, the aberration amount somewhat changes accordingly. In the apparatus as illustrated in the present embodiment, the memory 154 included in the controller 151 already stores the aberration information of the eye of the subject photographed by the fundus image photographing apparatus, for each photographing area of the eye to be inspected and for each resolution during photographing.

Figure 14:
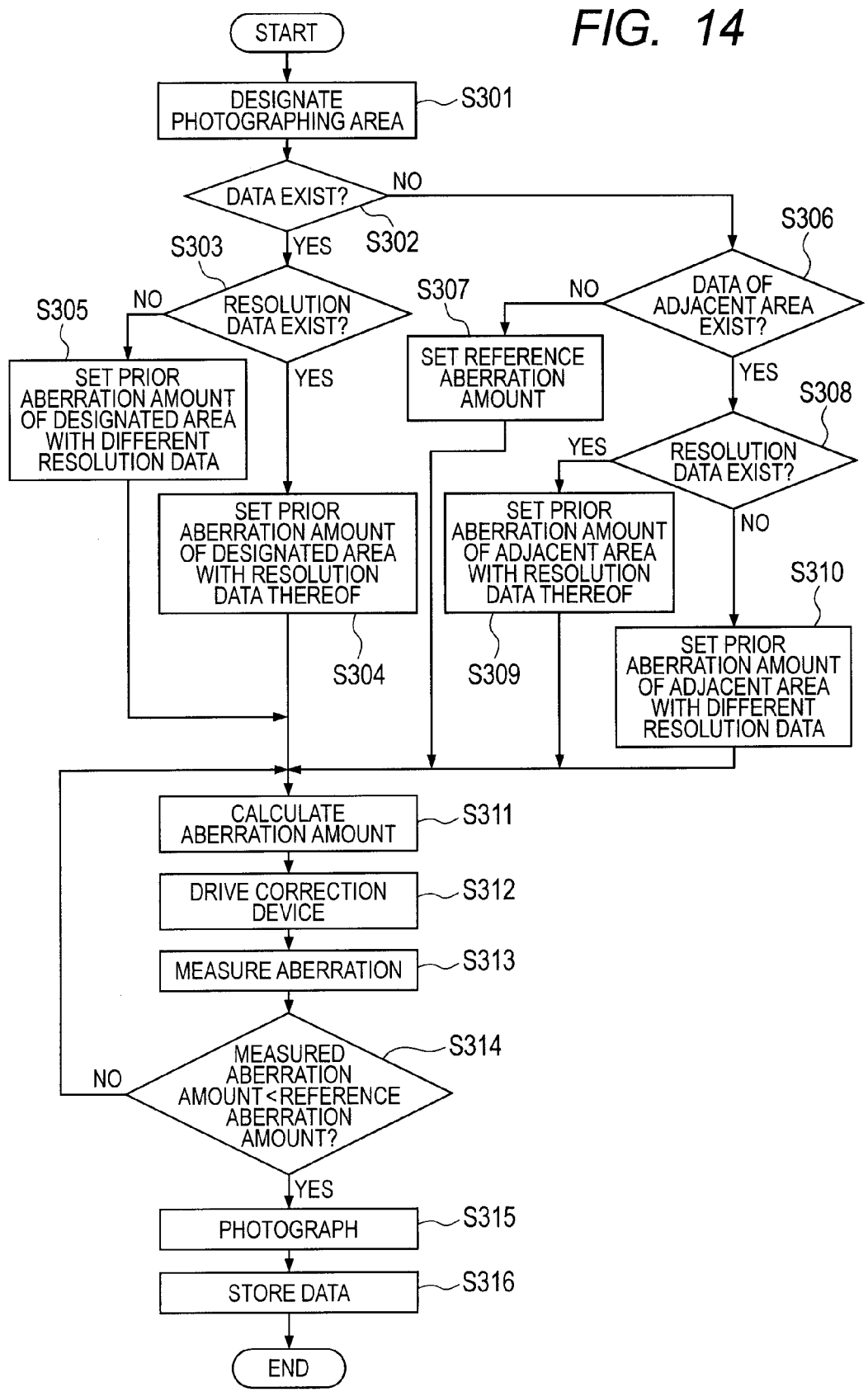
FIG. 14 is a flow chart illustrating a control step of the fundus image photographing apparatus according to the third embodiment of the present invention.

An operation of the present invention in the fundus image photographing apparatus with the configuration illustrated in FIG. 13 will be described with reference to a flow chart of FIG. 14. The same operation as in the first and second embodiments will not be described.

First, a mouse, a keyboard and a bar code reader not illustrated are used to designate the photographing area of the eye to be inspected and the resolution of the photographed image for the subject (S301). Whether the photographing area designated in S301 has been photographed is determined for the subject (S302). If the designated area has been photographed in the past, whether the designated area has been photographed with the designated resolution is determined (S303). If the designated area has been photographed with the designated resolution, the aberration amount of the last photographing for the designated area and the designated resolution is set to the adaptive optics control unit 116 (S304). If the designated area has not been photographed with the designated resolution, the aberration amount of the last photographing for the designated area and a different resolution is set to the adaptive optics control unit 116 (S305).

If the designated area has not been photographed, whether an adjacent area of the designated area has been photographed is determined this time (S306). If the adjacent area has not been photographed, the reference aberration amount is set to the adaptive optics control unit 116 (S307). If the adjacent area has been photographed, whether the adjacent area has been photographed with the designated resolution is determined (S308). If the adjacent area has been photographed with the designated resolution, the aberration amount of the last photographing for the adjacent area and the designated resolution is set to the adaptive optics control unit 116 (S309). If the adjacent area has not been photographed with the designated resolution, the aberration amount of the last photographing for the adjacent area and a different resolution is set to the adaptive optics control unit 116 (S310). The case of first photographing of the subject is processed in the same way as the case in which the designated area and the adjacent area of the designated area have not been photographed in the past. The process of S311 to S316 is the same as in the first and second embodiments.

According to the present third embodiment, the aberration information of the past photographing for the adjacent area of the designated area and the designated resolution can be used to reduce the time required for the aberration correction, and photographing is possible in a short time.

(Other Embodiments)

The present invention is also realized by executing the following process. More specifically, software (program) that realizes the functions of the embodiments is supplied to a system or an apparatus through a network or various storage media, and a computer (or a CPU or an MPU) of the system or the apparatus reads and executes the program in the process.

The present invention is not limited to the embodiments, and various modifications and changes can be made without departing from the scope of the present invention. For example, although the object is an eye in the embodiments, the present invention can also be applied to objects other than the eye, such as skin and organs. In this case, the present invention has a function of a medical instrument other than the ophthalmic apparatus, such as an endoscope. Therefore, it is desirable that the present invention is figured out as an inspection apparatus exemplified by the ophthalmic apparatus, and it is desirable that the eye to be inspected is figured out as a mode of the object. At the same time, the aberration correction apparatus may be built as a photographing apparatus of the eye to be inspected with the same configuration.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-105386, filed May 10, 2011, which is hereby incorporated by reference herein in its entirety.

What is claimed is:

1. An aberration correction apparatus for correcting an aberration of an eye to be inspected, the apparatus comprising:
   an aberration correction unit configured to correct the aberration of the eye to be inspected; and
   a memory unit configured to store information in which control information for controlling the aberration correction unit is associated with an address of an area in the eye to be inspected where the control information is acquired,
   wherein the aberration correction unit corrects the aberration of the eye to be inspected based on the information stored within the memory unit.

2. An aberration correction apparatus according to claim 1, wherein the control information includes aberration information of the eye to be inspected.

3. An aberration correction apparatus according to claim 1, wherein the information includes the control information, the address of the area in the eye to be inspected, and identification information of the eye to be inspected.

4. An aberration correction apparatus according to claim 1, further comprising:
   a photographing unit configured to photograph the eye to be inspected;
   an acquiring unit configured to acquire the photographed area which is photographed by the photographing unit; and
   a control information acquiring unit configured to acquire the control information corresponding to the photographed area acquired by the acquiring unit, among the information stored within the memory unit,
   wherein the aberration correction unit corrects the aberration of the eye to be inspected based on the information acquired by the control information acquiring unit.

5. An aberration correction apparatus according to claim 4, wherein the control information acquiring unit acquires the control information corresponding to the photographing area, when the control information corresponding to the photographing area acquired by the acquiring unit is included within the information stored within the memory unit, and
   wherein the control information acquiring unit acquires a previously determined control information, when the control information corresponding to the photographing area acquired by the acquiring unit is not included within the information stored within the memory unit.

6. An aberration correction apparatus according to claim 4, wherein the control information acquiring unit acquires the control information corresponding to the photographing area, when the control information corresponding to the photographing area acquired by the acquiring unit is included within the information stored within the memory unit, and
   wherein the control information acquiring unit acquires a control information corresponding to an adjacent area close to the photographed area, when the control information corresponding to the photographing area acquired by the acquiring unit is not included within the information stored within the memory unit.

7. An aberration correction apparatus according to claim 6, wherein the adjacent area is an area closest to the photographed area.

8. An aberration correction apparatus according to claim 1, further comprising an aberration measuring unit configured to measure an amount of the aberration of the eye to be inspected based on a return light from the eye to be inspected, which is generated from a light irradiated on the eye to be inspected,
   wherein after controlling based on the control information acquired from the information stored within the memory unit, the aberration correction unit corrects the aberration of the eye to be inspected until a measured amount of the aberration becomes smaller than a predetermined value.

9. An aberration correction apparatus according to claim 1, further comprising:
   an aberration measuring unit configured to measure an amount of the aberration of the eye to be inspected based on a return light from the eye to be inspected, which is generated from a light irradiated on the eye to be inspected; and
   a photographing unit configured to photograph the eye to be inspected,
   wherein the aberration correction unit corrects the aberration of the eye to be inspected until a measured amount of the aberration becomes smaller than a predetermined value, and
   wherein the photographing unit photographs the eye to be inspected after the measured amount of the aberration becomes smaller than the predetermined value.

10. An aberration correction apparatus according to claim 1, wherein the aberration correction unit corrects the aberration of the eye to be inspected using the control information acquired from the information stored within the memory unit.

11. An aberration correction apparatus according to claim 1, wherein an image of the eye to be inspected is divided into a grid, and
   wherein the address corresponds to a horizontal division of the grid or a vertical division of the grid.

12. An aberration correction apparatus according to claim 11, wherein the address corresponds to a horizontal division of the grid and a vertical division of the grid.

13. An aberration correction apparatus for correcting an aberration of an eye to be inspected, the apparatus comprising:
- an aberration correction unit configured to correct the aberration of the eye to be inspected; and
- a memory unit configured to store information in which control information for controlling the aberration correction unit is associated with an address of an area in a fundus of the eye to be inspected where the aberration of the eye to be inspected is acquired,
- wherein the aberration correction unit corrects the aberration of the eye to be inspected based on the information stored within the memory unit.

14. An aberration measurement apparatus for measuring an aberration of an eye to be inspected, the apparatus comprising:
- an aberration measurement unit configured to measure the aberration of the eye to be inspected; and
- a memory unit configured to store an address of an area in the eye to be inspected where aberration is measured and aberration information designating the aberration measured by the aberration measurement unit, the address being associated with the aberration information.

15. An aberration measurement apparatus according to claim 14, wherein the memory unit associates the address of the area in a fundus of the eye to be inspected with the aberration measured by the measurement unit, and stores the address and the measured aberration.

16. An aberration correction method for correcting an aberration of an eye to be inspected, the method comprising the steps of:
- storing, within a memory unit, information in which control information for controlling an aberration correction unit is associated with an address of an area in the eye to be inspected where the control information is acquired; and
- correcting, by the aberration correction unit, the aberration of the eye to be inspected based on the information stored within the memory unit.

17. A non-transitory tangible medium having recorded thereon a program for causing a computer to perform steps of the method according to claim 16.

18. An aberration correction method for correcting an aberration of an eye to be inspected, the method comprising the steps of:
- storing, by a memory unit, information in which control information for controlling an aberration correction unit is associated with an address of an area in a fundus of the eye to be inspected where the control information is acquired; and
- correcting, by the aberration correction unit, the aberration of the eye to be inspected based on the information stored within the memory unit.

19. A non-transitory tangible medium having recorded thereon a program for causing a computer to perform steps of the method according to claim 18.

20. An aberration measurement method for measuring an aberration of an eye to be inspected, the method comprising the steps of:
- measuring the aberration of the eye to be inspected; and
- storing an address of an area in the eye to be inspected where aberration is measured and an aberration information designating the measured aberration, the address being associated with the aberration information.

21. A non-transitory tangible medium having recorded thereon a program for causing a computer to perform steps of the method according to claim 20.

22. An aberration correction apparatus for correcting an aberration of an eye to be inspected, the apparatus comprising:
- a memory unit configured to store information in which the aberration of the eye to be inspected is associated with an address of an area in a fundus of the eye to be inspected where the aberration of the eye to be inspected is acquired; and
- an aberration correction unit configured to correct the aberration of the eye to be inspected based on the information stored within the memory unit.

23. An aberration correction method for correcting an aberration of an eye to be inspected, the method comprising the steps of:
- storing, within a memory unit, information in which the aberration of the eye to be inspected is associated with an address of an area in a fundus of the eye to be inspected where the aberration of the eye to be inspected is acquired; and
- correcting the aberration of the eye to be inspected based on the information stored within the memory unit.

24. A non-transitory tangible medium having recorded thereon a program for causing a computer to perform steps of the method according to claim 23.

* * * * *